United States Patent
Oota et al.

(10) Patent No.: US 7,663,006 B2
(45) Date of Patent: Feb. 16, 2010

(54) PROCESS FOR PRODUCTION OF PURIFIED ALCOHOLS

(75) Inventors: Hirofumi Oota, Kurashiki (JP); Hiroki Kawasaki, Kurashiki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 169 days.

(21) Appl. No.: 10/592,699

(22) PCT Filed: Mar. 14, 2005

(86) PCT No.: PCT/JP2005/004454

§ 371 (c)(1),
(2), (4) Date: Jan. 16, 2007

(87) PCT Pub. No.: WO2005/087694

PCT Pub. Date: Sep. 22, 2005

(65) Prior Publication Data

US 2008/0242899 A1   Oct. 2, 2008

(30) Foreign Application Priority Data

Mar. 16, 2004   (JP) ............................. 2004-073958

(51) Int. Cl.
*C07C 29/141*   (2006.01)
(52) U.S. Cl. ...................................... 568/881; 568/883
(58) Field of Classification Search ................. 568/881, 568/883
See application file for complete search history.

(56) References Cited

U.S. PATENT DOCUMENTS 5,475,161 A    12/1995   Horn et al.

FOREIGN PATENT DOCUMENTS

JP    2 124839    5/1990
JP    3 120234    5/1991

*Primary Examiner*—Elvis O Price
(74) *Attorney, Agent, or Firm*—Oblon, Spivak, McClelland, Maier & Neustadt, L.L.P.

(57) ABSTRACT

A process for producing a purified alcohol giving satisfactory results in a sulfuric acid coloring test is provided.

A process for producing a purified alcohol which includes the following steps:
  a condensation step in which an aldehyde is subjected to aldol condensation and dehydration to obtain the corresponding condensate,
  a hydrogenation step in which the condensate is hydrogenated to obtain a crude alcohol, and
  a purification step in which the crude alcohol is distilled to obtain a purified alcohol,
  characterized in that the crude alcohol in which the concentration of one or more compounds having an oxygen-containing heterocycle having a carbon-carbon double bond in the ring is 200 weight ppm or lower is fed to the purification step. Specifically, the aldehyde is normal butyraldehyde, the condensate is 2-ethylhexenal, and the alcohol is 2-ethylhexanol.

15 Claims, 1 Drawing Sheet

PROCESS FOR PRODUCTION OF PURIFIED ALCOHOLS

TECHNICAL FIELD

The present invention relates to a process for producing an alcohol by subjecting an aldehyde to condensation and dehydration reactions to produce a condensate thereof and hydrogenating the condensate. More particularly, the invention relates to a process in which normal butyraldehyde (NBD) is subjected to condensation and dehydration reactions to produce 2-ethylhexenal (EPA) and this compound is hydrogenated to thereby produce 2-ethylhexanol (2EH).

BACKGROUND ART

The production of 2-ethylhexanol (2EH) from normal butyraldehyde (NBD) is being industrially conducted on a large scale. This process is constituted of an NBD condensation step in which two molecules of NBD undergo aldol condensation and dehydration to give 2-ethylhexenal (ethylpropylacrolein, EPA), an EPA hydrogenation step in which the EPA obtained is reacted with hydrogen to obtain crude 2EH, and a 2EH purification step in which the crude 2EH is purified to a desired purity to obtain a 2EH product. The purification of crude 2EH is conducted mainly by distillation.

Although it is a matter of course that alcohols including 2EH as industrial products which are dealt in on the market should have a high purity, these alcohols are also required to be reduced in coloring in a sulfuric acid coloring test.

Substances which have been conventionally known to cause 2EH to give unfavorable results in a sulfuric acid coloring test are aldehydes such as 2-ethylhexanal (2HA) and unsaturated alcohols such as 2-ethylhexenal. For example, patent document 1 discloses a process for producing a saturated alcohol by reacting the corresponding aldehyde in a vapor phase with hydrogen, wherein a product of the reduction of a catalyst precursor composition containing an ingredient represented by the following general formula (i) is used as a hydrogenation catalyst to thereby diminish unsaturated alcohols in 2EH.

[Formula-1]

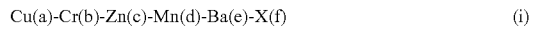

Cu(a)-Cr(b)-Zn(c)-Mn(d)-Ba(e)-X(f)    (i)

(In the formula, X represents a transition metal in Group 8 or Group 4A of the periodic table, and a to f, which represent the contents of the respective components in terms of oxide amount, are as follows: a indicates 20-50% by weight, b 0-50% by weight, c 0-50% by weight, d 0.1-5.0% by weight, e 0.1-5.0% by weight, and f 0.01-3.0% by weight.)

However, there are cases where even 2EH from which aldehydes and unsaturated alcohols have been removed gives poor results in a sulfuric acid coloring test.

Patent Document 1: JP-A-8-3084

DISCLOSURE OF THE INVENTION

Problem that the Invention is to Solve

Accordingly, an object of the invention is to provide a process for producing a purified alcohol (in particular, 2EH) which gives satisfactory results in a sulfuric acid coloring test.

Means for Solving the Problem

Investigations made by the present inventors revealed that when compounds having a heterocycle having a carbon-carbon double bond therein, such as a pyran ring or dihydropyran ring, are present in an alcohol, this alcohol gives unfavorable results in a sulfuric acid coloring test. Although these compounds can be separated in some degree from the alcohol by distillation, the separation thereof by ordinary distillation is extremely difficult. It is important to reduce beforehand the amount of those compounds present in the crude alcohol to be subjected to a purification treatment. For obtaining an alcohol product giving satisfactory results in a sulfuric acid coloring test, it is desirable to reduce beforehand the concentration of those compounds in the crude alcohol to 200 weight ppm or lower, especially 100 weight ppm or lower. As a result of investigations made by the inventors, one method effective in reducing the amount of those compounds present in a crude alcohol was found to comprise distilling a reaction product obtained by the condensation and dehydration of an aldehyde to obtain the condensate as a distillate and thereby separate high-boiling compounds and feeding the condensate to a hydrogenation step. Furthermore, the amount of those compounds in a crude alcohol can be reduced also by hydrogenating the condensate in two stages by conducting catalytic hydrogenation and catalytic hydrogenation in which a catalyst different from that in the former hydrogenation is used.

The invention has been achieved based on such findings. Essential points of the invention reside in the following (1) to (8).

(1) A process for producing a purified alcohol which comprises the following steps:

a condensation step in which an aldehyde is subjected to aldol condensation and dehydration to obtain the corresponding condensate, a hydrogenation step in which the condensate is hydrogenated to obtain a crude alcohol, and a purification step in which the crude alcohol is distilled to obtain a purified alcohol, characterized in that the crude alcohol in which the concentration of one or more compounds having an oxygen-containing heterocycle having a carbon-carbon double bond in the ring is 200 weight ppm or lower is fed to the purification step.

(2) The production process as described under (1) above wherein the aldehyde is normal butyraldehyde, the condensate is 2-ethylhexenal, and the alcohol is 2-ethylhexanol.

(3) The production process as described under (1) or (2) above characterized in that the crude alcohol in which the concentration of one or more compounds having an oxygen-containing heterocycle having a carbon-carbon double bond in the ring is 100 weight ppm or lower is fed to the purification step.

(4) The production process as described under any one of (1) to (3) above characterized in that the one or more compounds having an oxygen-containing heterocycle having a carbon-carbon double bond in the ring are compounds having a pyran ring or dihydropyran ring.

(5) The production process as described under any one of (1) to (4) above characterized in that the condensate obtained in the condensation step is fed to the hydrogenation step after the content of high-boiling compounds in the condensate is reduced.

(6) The production process as described under any one of (1) to (5) above characterized in that the hydrogenation step is conducted using at least two kinds of catalysts.

(7) The production process as described under any one of (1) to (5) above characterized in that the hydrogenation step is conducted in two stages by conducting a vapor-phase hydrogenation step and a liquid-phase hydrogenation step in which a catalyst different from that in the vapor-phase hydrogenation step is used.

(8) The production process as described under any one of (1) to (7) above characterized in that the purified alcohol obtained by the purification step shows a coloring of 30 APHA or lower in a sulfuric acid coloring test.

ADVANTAGE OF THE INVENTION

According to the invention, a purified alcohol giving satisfactory results in a sulfuric acid coloring test can be produced.

BEST MODE FOR CARRYING OUT THE INVENTION

Figure 1:
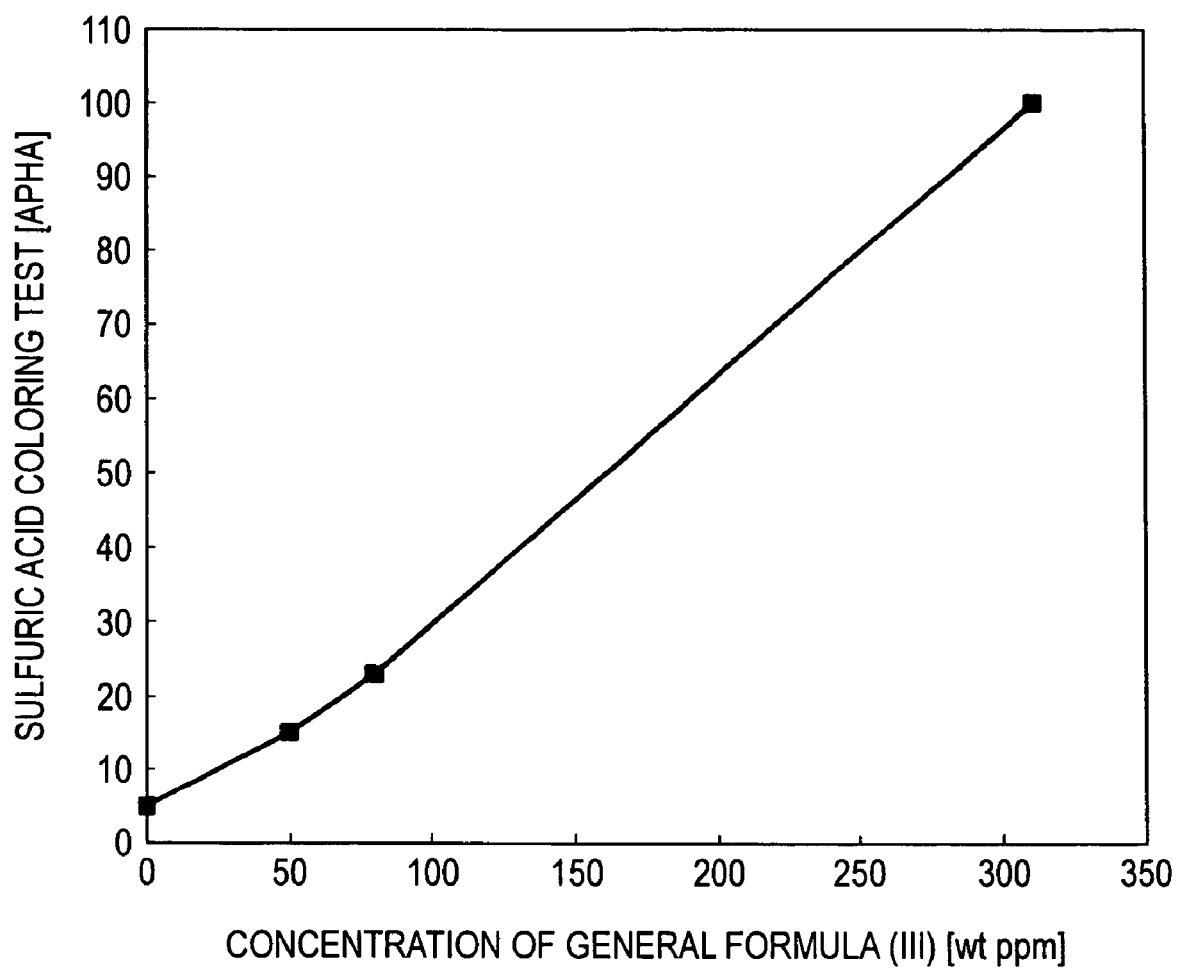
FIG. 1 is a presentation showing the results of Example 2.

In the invention, an aldehyde is first subjected to aldol condensation and dehydration reactions to obtain a condensate. The aldehyde is not particularly limited, and use may be made of a saturated aldehyde having at least 3 carbon atoms, generally 3-10 carbon atoms. Examples of the saturated aldehyde include linear and branched aldehydes. Specific examples thereof include propionaldehyde, butyraldehyde, valeraldehyde, heptylaldehyde, and nonyl aldehyde. Preferred are butyraldehyde and valeraldehyde. Especially preferred is normal butyraldehyde. Examples of the condensate include the condensates corresponding to the aldehydes shown above. Specific examples thereof include 2-methylpentenal, 2-ethylhexenal, and 2-propylheptenal. Preferred are 2-ethylhexenal and 2-propylheptenal. Especially preferred is 2-ethylhexenal (ethylpropylacrolein). This condensation reaction and dehydration can be conducted by a known method. In general, the condensation and dehydration are conducted by reacting the aldehyde generally at 80-100° C. using an aqueous alkali solution, e.g., a 1-5 wt % aqueous solution of sodium hydroxide, as a catalyst.

The liquid reaction mixture is separated into an aqueous phase comprising the aqueous alkali solution and an oil phase comprising the condensate. The aqueous phase is circulated and used as a catalyst.

Investigations made by the inventors revealed that the condensate obtained in the condensation step contains a compound having a carbon-carbon double bond. Specifically, in the case where the starting aldehyde is normal butyraldehyde, the 2-ethylhexanal obtained in the condensation step contains the aldehyde compound of the following formula (I) which is thought to have been generated by the condensation of three NBD molecules.

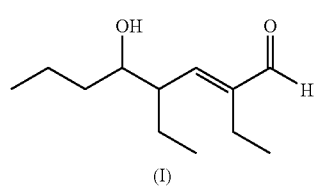

(I)

[Formula -2]

It is presumed that in the subsequent hydrogenation step, this compound is converted to the compound (II) having a pyran ring and part of the compound (II) is hydrogenated to the compound (III) having a dihydropyran ring. Even when contained in an extremely slight amount, these compounds cause the alcohol to give considerably unfavorable results in a sulfuric acid coloring test.

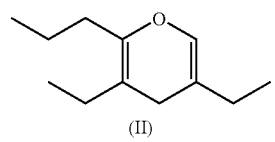

(II)

[Formula-3]

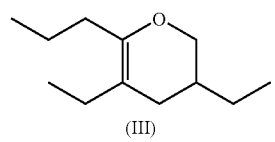

(III)

[Formula-4]

The compounds having an oxygen-containing heterocycle having a carbon-carbon double bond in the ring (the compounds (II) and (III)) can be converted by hydrogenation to the corresponding compound having a tetrahydropyran ring. This compound yielded, which has a tetrahydropyran ring, does not cause the alcohol to give unfavorable results in a sulfuric acid coloring test. However, under ordinary conditions for the hydrogenation of the condensate (2-ethylhexenal), it is difficult to completely hydrogenate the compounds having an oxygen-containing heterocycle having a carbon-carbon double bond in the ring (compounds (II) and (III)) to the compound having a tetrahydropyran ring. Consequently, when the condensate (2-ethylhexenal) which has been obtained by the condensation reaction and dehydration of NBD and contains a high-boiling compound (the compound (I)) is hydrogenated without any treatment, then the crude alcohol yielded (2EH) contains the compounds (the compounds (II) and (III)) having an oxygen-containing heterocycle having a carbon-carbon double bond in the ring, which remains without being hydrogenated to a tetrahydropyran ring. Since these compounds are difficult to be separated from the alcohol (2EH) by ordinary distillation, they come into the product alcohol (2EH) to cause it to give unfavorable results in a sulfuric acid coloring test. It is therefore desirable that the total concentration of compounds having an oxygen-containing heterocycle having a carbon-carbon double bond in the ring (compounds having a pyran ring or dihydropyran ring) in the alcohol (2EH) to be subjected to the purification step be reduced beforehand to 200 weight ppm or lower, preferably 100 weight ppm or lower, especially preferably 50 weight ppm or lower.

Examples of methods for reducing the concentration of compounds having an oxygen-containing heterocycle having a carbon-carbon double bond in the ring (compounds having a pyran ring or dihydropyran ring) in the crude alcohol include distillation techniques such as rectification and flash distillation. Specific examples thereof include a method in which the condensate obtained in the aldehyde condensation step is distilled to separate the high-boiling compounds generated by the condensation (the compound (I)) from the condensate together with other high-boiling compounds and the condensate reduced in high-boiling-compound concentration is subjected to the subsequent hydrogenation step. The distillation can be conducted, for example, with a distillation column having about 5-20 plates under the conditions of a column top temperature of 80-200° C. and a column top pressure of from 90 mmHg to atmospheric pressure. This operation may be conducted at a reflux ratio of 0.2-10, preferably 0.2-5, or while purging 3-10% of the feed amount through the bottom of the distillation column, whereby the degree of removal of high-boiling compounds from the condensate obtained in the condensation step can be heightened to 98% or above. In case where a condensate containing high-boiling compounds is fed to a hydrogenation step, there is a possibility that the high-boiling compounds might yield compounds having an oxygen-containing heterocycle having a carbon-carbon double bond in the ring (the compounds (II) and (III)) during the step. However, when the condensate in which the concentration of high-boiling compounds has been reduced is subjected to hydrogenation, then the generation of compounds having an oxygen-containing heterocycle having a carbon-carbon double bond in the ring (the compounds (II) and (III)) in the hydrogenation step can be avoided.

The hydrogenation reaction of the condensate reduced in high-boiling-compound concentration can be conducted in either a vapor phase or a liquid phase. As a catalyst may be used one obtained by depositing an active ingredient such as nickel, chromium, copper, or palladium on a support such as diatomaceous earth, zeolite, alumina, or active carbon. It is especially preferred to use one obtained by depositing nickel and chromium on diatomaceous earth or one obtained by reducing an oxide of chromium, copper, zinc, manganese, barium, etc. The reaction temperature and pressure may be selected in the ranges of 40-200° C. and of from atmospheric pressure to about 15.0 MPa according to the catalyst and reaction mode to be used.

Another method for reducing the concentration of compounds having an oxygen-containing heterocycle having a carbon-carbon double bond in the ring (compounds having a pyran ring or dihydropyran ring) in the crude alcohol is to hydrogenate the high-boiling compounds generated by the condensation (the compound (I)) and the compounds having an oxygen-containing heterocycle having a carbon-carbon double bond in the ring (the compounds (II) and (III)) to the corresponding compounds having a tetrahydropyran ring when the condensate (2-ethylhexenal) is hydrogenated. However, it is difficult with one kind of catalyst to simultaneously and efficiently conduct the hydrogenation of the condensate (2-ethylhexenal) to an alcohol (2EH) and the hydrogenation of the high-boiling compounds generated by the condensation (the compound (I)) and the compounds having an oxygen-containing heterocycle having a carbon-carbon double bond in the ring (the compounds (II) and (III)) to the corresponding compounds having a tetrahydropyran ring. Consequently, in order that the high-boiling compounds generated by the condensation (the compound (I)) and the compounds having an oxygen-containing heterocycle having a carbon-carbon double bond in the ring (the compounds (II) and (III)) might be hydrogenated to the corresponding compounds having a tetrahydropyran ring in the step of hydrogenating the condensate (2-ethylhexenal), reaction conditions including the catalyst, temperature, and pressure may be regulated so as to be suitable for each of the hydrogenation of the condensate (2-ethylhexenal) and the hydrogenation of the compounds having a pyran ring or dihydropyran ring to the corresponding compounds having a tetrahydropyran ring.

Examples of such reaction conditions include: a method in which a first-stage hydrogenation reaction is conducted at 100-200° C. and a pressure of from atmospheric pressure to 15.0 MPa using a Cu—Cr catalyst and a second-stage hydrogenation reaction is subsequently conducted at 50-150° C. and 2.0-5.0 MPa using a nickel catalyst; and a method in which a first-stage hydrogenation reaction is conducted at 100-200° C. and a pressure of from atmospheric pressure to 15.0 MPa using an Ni—Cr catalyst and a second-stage hydrogenation reaction is subsequently conducted at 50-150° C. and 2.0-5.0 MPa using a $Pd/Al_2O_3$ catalyst. The first-stage and second-stage hydrogenation reactions each independently may be either vapor-phase hydrogenation or liquid-phase hydrogenation. Examples include "a method in which the first-stage hydrogenation reaction is a vapor-phase reaction and the second-stage hydrogenation is a vapor-phase reaction", "a method in which the first-stage hydrogenation reaction is a liquid-phase reaction and the second-stage hydrogenation is a liquid-phase reaction", and "a method in which the first-stage hydrogenation reaction is a vapor-phase reaction and the second-stage hydrogenation is a liquid-phase reaction". From the standpoint of heat recovery, it is preferred that the first-stage hydrogenation reaction be conducted in a vapor phase. From the standpoint of reducing the generation of by-products, it is preferred to conduct the second-stage hydrogenation reaction in a liquid phase under mild conditions.

The second-stage hydrogenation reaction should be conducted using a reactor having a fixed bed in such a manner that the hydrogenation reaction is conducted under "conditions suitable for the hydrogenation of the condensate" up to a place in the middle of the catalyst layer and that after the place in the middle of the catalyst layer, the hydrogenation reaction is conducted under "conditions suitable for the hydrogenation of the high-boiling compounds generated by condensation (the compound (I)) and compounds having an oxygen-containing heterocycle having a carbon-carbon double bond in the ring (compounds (II) and (III)) to the corresponding compounds having a tetrahydropyran ring". Specifically, this can be accomplished by regulating the temperature of the feed being sent to the second-stage reactor so that the feed has a necessary temperature in the area which should have the "conditions suitable for the hydrogenation of the high-boiling compounds generated by condensation (the compound (I)) and compounds having an oxygen-containing heterocycle having a carbon-carbon double bond in the ring (compounds (II) and (III)) to the corresponding compounds having a tetrahydropyran ring", or by regulating the catalyst amount so that a necessary residence time in the area having the "conditions suitable for the hydrogenation of the high-boiling compounds generated by condensation (the compound (I)) and compounds having an oxygen-containing heterocycle having a carbon-carbon double bond in the ring (compounds (II) and (III)) to the corresponding compounds having a tetrahydropyran ring" can be maintained. This operation can heighten the degree of hydrogenation of the condensate (specifically to 98% or higher) and reduce the concentration of compounds having an oxygen-containing heterocycle having a carbon-carbon double bond in the ring (compounds having a pyran ring or dihydropyran ring) to or below the target value.

The term "a place in the middle of the catalyst layer" as used above specifically means a place at which the degree of hydrogenation of the condensate becomes 98% or higher and after which the reaction mixture has a catalyst contact time of 5 minutes or longer in the case of liquid-phase hydrogenation or of 0.3 seconds or longer in the case of vapor-phase hydrogenation. Control for obtaining the conditions suitable for each of the hydrogenation operations may be accomplished by regulating the temperature of the reactor inlet or adding a solvent for heat removal.

In the case of liquid-phase hydrogenation, it is preferred to regulate the superficial linear velocity in the reactor to 10 m/hr or higher in order to inhibit channeling in the reactor.

Whichever method described above is used, the concentration of compounds having an oxygen-containing heterocycle having a carbon-carbon double bond in the ring (compounds having a pyran ring or dihydropyran ring) in the crude alcohol (2EH) obtained by the hydrogenation can be 200 weight ppm or lower, especially 100 weight ppm or lower. In the invention, the crude alcohol (2EH), which has such a low content of compounds having an oxygen-containing heterocycle having a carbon-carbon double bond in the ring (compounds having a pyran ring or dihydropyran ring), is distilled to obtain a purified alcohol (2EH) as a product. In the invention, this alcohol to be subjected to distillation is referred to as "crude alcohol", and the step of distilling the crude alcohol to obtain purified alcohol is the "purification step" in the invention. The alcohol obtained through the distillation is referred to as "purified alcohol" in the invention. Examples of the distillation in the invention include rectification and flash distillation. This distillation may be conducted by an ordinary method. For example, it may be conducted using a distillation column having 20-50 plates at a column top pressure of from 50 mmHg to atmospheric pressure in such a manner that the purified 2EH obtained as a distillate has a purity of 99.5% or higher, preferably 99.8% or higher. With respect to pressure in this distillation operation, however, it is desirable to conduct the operation under a higher vacuum from the standpoint of the generation of by-products in the distillation column and for using a more inexpensive low-pressure vapor to conduct the distillation.

According to the invention, purified 2EH which shows a coloring of 30 APHA or lower, especially 20 APHA or lower, in a sulfuric acid coloring test can be easily obtained. The sulfuric acid coloring test is as follows.

Into a dry 300-mL ground-stopper flat bottom flask is introduced 100 mL of a sample. While the sample is being stirred, 8 mL of 98 wt % concentrated sulfuric acid is added thereto at a rate of 2 mL/min at a room temperature of 30° C. or lower. Subsequently, the flask is stoppered and immersed for 2 hours in a water bath of 98±2° C. This flask is cooled to room temperature with water. Thereafter, 100 mL of the sample is introduced into a flat-bottom color comparison tube made of glass having an inner diameter of 25 mm and a height of 270 mm, and is visually compared with APHA color standard solutions each placed in an amount of 100 mL in the same color comparison tube. The APHA value for the color standard solution which has the same color as the sample is taken as a measured value.

The APHA color standard solutions are prepared in the following manner. The ingredients shown below are dissolved in distilled water so as to precisely result in a total amount of 1,000 mL. This solution is referred to as APHA 500.

| | |
|---|---|
| Potassium chloroplatinate ($K_2PtCl_6$) | 1.245 g |
| Cobalt chloride ($CoCl_2/6H_2O$) | 1.000 g |
| 98% Concentrated sulfuric acid | 100 mL |

This APHA 500 color standard solution is diluted with distilled water to produce color standard solutions having various APHA values. For examples, diluting the APHA 500 color standard solution with distilled water so as to double the volume of the solution gives an APHA 250 color standard solution.

The invention will be explained in detail by reference to Examples.

Example 1

Normal butyraldehyde was mixed with 2 wt % aqueous sodium hydroxide solution and reacted at 90° C. The liquid reaction mixture was allowed to stand and separate into layers to thereby obtain 2-ethylhexenal.

The 2-ethylhexenal obtained was distilled with a distiller having 10 Oldshue plates under the conditions of a column top pressure of 200 mmHg and a reflux ratio of 0.23 to remove 99% of the high-boiling compounds. This 2-ethylhexenal from which high-boiling compounds had been removed was subjected to liquid-phase hydrogenation at a temperature of 120° C. and a pressure of 4.0 MPa in the presence of an Ni—Cr catalyst to thereby obtain crude 2EH. This crude 2EH contained 8 weight ppm dihydropyran compound and 0 weight ppm pyran compound.

This crude 2EH was distilled with a distiller having 35 Oldshue plates under the conditions of a column top pressure of 100 mmHg and a reflux ratio of 7 to thereby remove low-boiling compounds from the crude 2EH. The crude 2EH was successively distilled at a column top pressure of 100 mmHg to thereby remove high-boiling compounds from the crude 2EH. Thus, the crude 2EH was purified. The purified 2EH obtained had a purity of 99.9%, a dihydropyran compound concentration of 1.4 weight ppm, and a pyran compound concentration of 0 weight ppm. In the sulfuric acid coloring test, this purified 2EH showed a coloring of 5 APHA.

Example 2

The crude 2EH obtained in Example 1 was distilled to obtain purified 2EH having a dihydropyran compound concentration of 0 weight ppm and a pyran compound concentration of 0 weight ppm. The dihydropyran compound represented by general formula (III) was added to this purified 2EH in various concentrations. The resultant solutions were subjected to the sulfuric acid coloring test. The results obtained are shown in Table 1.

TABLE 1

| Concentration of general formula (III) in 2EH (weight ppm) | Sulfuric acid coloring test (APHA) |
|---|---|
| 0 | 5 |
| 50 | 15 |
| 80 | 23 |
| 310 | 100 |

FIG. 1 was drawn from the results given in Table 1. When this FIGURE is used, the results of the sulfuric acid coloring test can be determined from the concentration of the compound of general formula (III) in the 2EH.

Example 3

Normal butyraldehyde was mixed with 2 wt % aqueous sodium hydroxide solution and reacted at 90° C. The liquid reaction mixture was allowed to stand and separate into layers to thereby obtain 2-ethylhexenal.

The 2-ethylhexenal obtained was subjected to vapor-phase hydrogenation at a temperature of 190° C. and a pressure of 0.45 MPa in the presence of a Cu—Cr—Mn—Ba—Ni catalyst (nickel content, 1%) to react about 90% of the 2-ethylhexenal.

This liquid hydrogenation reaction mixture was vaporized and fed, together with hydrogen gas, to a fixed-bed reactor packed with an Ni—Zr catalyst. The feed temperature was regulated so that the temperature as measured at a place located in the ¾ position from the inlet of the catalyst layer became 140° C. Vapor-phase hydrogenation was conducted at a pressure of 0.45 MPa. This reaction was conducted while supplying the feed material at such a rate that the gas space velocity (GHSV) as measured in the catalyst layer after the ¾ position from the inlet became 10,000 $Hr^{-1}$ or lower. The crude 2EH obtained by this reaction had a dihydropyran compound concentration of 129 weight ppm and a pyran compound concentration of 0 weight ppm. Furthermore, the gas was sampled in the ¾ position from the inlet of the catalyst layer and condensed. The resultant liquid was analyzed by gas chromatography. As a result, 2-ethylhexenal was not detected and 100% of the 2-ethylhexenal feed was found to have been hydrogenated. This liquid had a dihydropyran compound concentration of 1,310 weight ppm and a pyran compound concentration of 0 weight ppm.

The step of distilling the crude 2EH to obtain purified 2EH in the same manner as in Example 1 was simulated to determine the pyran compound and dihydropyran compound concentrations in the purified 2EH. As a result, the purified 2EH obtained was found to have a purity of 99.9%, dihydropyran compound concentration of 67 weight ppm, and pyran compound concentration of 0 weight ppm. It can be seen from FIG. 1 that this purified 2EH shows a coloring of 20 APHA in the sulfuric acid coloring test.

Example 4

Normal butyraldehyde was mixed with 2 wt % aqueous sodium hydroxide solution and reacted at 90° C. The liquid reaction mixture was allowed to stand and separate into layers to thereby obtain 2-ethylhexenal.

The 2-ethylhexenal obtained was subjected to liquid-phase hydrogenation at a temperature of 120° C. and a pressure of 4.0 MPa in the presence of an Ni—Cr catalyst to react about 90% of the 2-ethylhexenal.

This liquid hydrogenation reaction mixture was further fed to a fixed-bed reactor packed with a 5%-Pd/$Al_2O_3$ catalyst. The feed temperature was regulated so that the temperature as measured at a place located in the ¾ position from the inlet of the catalyst layer became 130° C. Liquid-phase hydrogenation was conducted at a pressure of 5.0 MPa. This reaction was conducted while supplying the feed material at such a rate that the residence time in the catalyst layer after the ¾ position from the inlet became 10 minutes or longer. The crude 2EH obtained by this reaction had a dihydropyran compound concentration of 0 weight ppm and a pyran compound concentration of 0 weight ppm. Furthermore, the liquid was sampled in the ¾ position from the inlet of the catalyst layer and analyzed by gas chromatography. As a result, 2-ethylhexenal was not detected and 100% of the 2-ethylhexenal feed was found to have been hydrogenated. This liquid had a dihydropyran compound concentration of 384 weight ppm and a pyran compound concentration of 0 weight ppm.

The step of distilling the crude 2EH to obtain purified 2EH in the same manner as in Example 1 was simulated to determine the pyran compound and dihydropyran compound concentrations in the purified 2EH. As a result, the purified 2EH obtained was found to have a purity of 99.9%, dihydropyran compound concentration of 0 weight ppm, and pyran compound concentration of 0 weight ppm. It can be seen from FIG. 1 that this purified 2EH shows a coloring of 5 APHA in the sulfuric acid coloring test.

Example 5

The step of distilling crude 2EH having a dihydropyran compound concentration of 200 weight ppm and a pyran compound concentration of 0 weight ppm to obtain purified 2EH in the same manner as in Example 1 was simulated to determine the pyran compound and dihydropyran compound concentrations in the purified 2EH. As a result, the purified 2EH obtained was found to have a purity of 99.9%, dihydropyran compound concentration of 105 weight ppm, and pyran compound concentration of 0 weight ppm. It can be seen from FIG. 1 that this purified 2EH shows a coloring of 30 APHA in the sulfuric acid coloring test.

Comparative Example 1

Normal butyraldehyde was mixed with 2 wt % aqueous sodium hydroxide solution and reacted at 90° C. The liquid reaction mixture was allowed to stand and separate into layers to thereby obtain 2-ethylhexenal.

The 2-ethylhexenal obtained was subjected to liquid-phase hydrogenation at a temperature of 120° C. and a pressure of 4.0 MPa in the presence of an Ni—Cr catalyst to thereby obtain crude 2EH. This crude 2EH contained 878 weight ppm dihydropyran compound and 0 weight ppm pyran compound.

The step of distilling the crude 2EH to obtain purified 2EH in the same manner as in Example 1 was simulated to determine the pyran compound and dihydropyran compound concentrations in the purified 2EH. As a result, the purified 2EH obtained was found to have a purity of 99.9%, dihydropyran compound concentration of 359 weight ppm, and pyran compound concentration of 0 weight ppm. It can be seen from FIG. 1 that this purified 2EH shows a coloring of 100 APHA in the sulfuric acid coloring test.

While the invention has been described in detail and with reference to specific embodiments thereof, it will be apparent to one skilled in the art that various changes and modifications can be made therein without departing from the spirit and scope thereof.

This application is based on a Japanese patent application filed on Mar. 16, 2004 (Application No. 2004-073958), the contents thereof being herein incorporated by reference.

INDUSTRIAL APPLICABILITY

According to the invention, a purified alcohol giving satisfactory results in a sulfuric acid coloring test can be produced.

The invention claimed is:

1. A process for producing a purified alcohol, comprising the following steps:
    a condensation step in which an aldehyde is subjected to aldol condensation and dehydration to obtain the corresponding condensate,
    a hydrogenation step in which the condensate is hydrogenated to obtain a crude alcohol, and
    a purification step in which the crude alcohol is distilled to obtain a purified alcohol showing a coloring of 30 APHA or lower in a sulfuric acid coloring test,
    wherein the crude alcohol in which the concentration of one or more compounds having an oxygen-containing heterocycle having a carbon-carbon double bond in the ring is 200 weight ppm or lower is fed to the purification step.

2. The production process of claim 1, wherein the aldehyde is normal butyraldehyde, the condensate is 2-ethylhexenal, and the alcohol is 2-ethylhexanol.

3. The production process of claim 1, wherein the crude alcohol in which the concentration of one or more compounds having an oxygen-containing heterocycle having a carbon-carbon double bond in the ring is 100 weight ppm or lower is fed to the purification step.

4. The production process of claim 1, wherein the one or more compounds having an oxygen-containing heterocycle having a carbon-carbon double bond in the ring is or are compounds having a pyran ring or dihydropyran ring.

5. The production process of claim 1, wherein the condensate obtained in the condensation step is fed to the hydrogenation step after the content of high-boiling compounds in the condensate is reduced.

6. The production process of claim 1, wherein the hydrogenation step is conducted using at least two kinds of catalysts.

7. The production process of claim 1, wherein the hydrogenation step is conducted in two stages by conducting a vapor-phase hydrogenation step and a liquid-phase hydrogenation step in which a catalyst different from that in the vapor-phase hydrogenation step is used.

8. A process for producing a purified alcohol, comprising the following steps:
   a condensation step in which an aldehyde is subjected to aldol condensation and dehydration to obtain the corresponding condensate,
   a hydrogenation step in which the condensate is hydrogenated to obtain a crude alcohol, and
   a purification step in which the crude alcohol is distilled to obtain a purified alcohol showing a coloring of 30 APHA or lower in a sulfuric acid coloring test,
   wherein
   the condensate in the condensation step is distilled and the condensate reduced in high-boiling-compound concentration is fed to the hydrogenation step,
   or
   the hydrogenation step is conducted using at least two kinds of catalysts to reduce the concentration of one or more compounds having an oxygen-containing heterocycle having a carbon-carbon double bond in the ring in the crude alcohol, the crude alcohol in which the concentration of said compounds having an oxygen-containing heterocycle having a carbon-carbon double bond in the ring is 200 weight ppm or lower is fed to the purification step.

9. The process of claim 8, wherein the condensate in the condensation step is distilled and the condensate reduced in high-boiling-compound concentration is fed to the hydrogenation step.

10. The process of claim 8, wherein the hydrogenation step is conducted using at least two kinds of catalysts to reduce the concentration of one or more compounds having an oxygen-containing heterocycle having a carbon-carbon double bond in the ring in the crude alcohol, the crude alcohol in which the concentration of said compounds having an oxygen-containing heterocycle having a carbon-carbon double bond in the ring is 200 weight ppm or lower is fed to the purification step.

11. The process of claim 8, wherein the aldehyde is normal butyraldehyde, the condensate is 2-ethylhexenal, and the alcohol is 2-ethylhexanol.

12. The process of claim 8, wherein the crude alcohol in which the concentration of one or more compounds having an oxygen-containing heterocycle having a carbon-carbon double bond in the ring is 100 weight ppm or lower is fed to the purification step.

13. The process of claim 8, wherein the one or more compounds having an oxygen-containing heterocycle having a carbon-carbon double bond in the ring is or are compounds having a pyran ring or dihydropyran ring.

14. The process of claim 8, wherein the hydrogenation step is conducted in two stages by conducting a vapor-phase hydrogenation step and a liquid-phase hydrogenation step in which a catalyst different from that in the vapor-phase hydrogenation step is used.

15. A process for producing a purified alcohol, comprising the following steps:
   a condensation step in which an aldehyde is subjected to aldol condensation and dehydration to obtain the corresponding condensate, and
   a purification step in which the crude alcohol is distilled to obtain a purified alcohol showing a coloring of 30 APHA or lower in a sulfuric acid coloring test,
   wherein
   the condensate in the condensation step is distilled and the condensate reduced in high-boiling-compound concentration is fed to the hydrogenation step,
   or
   the hydrogenation step is conducted using at least two kinds of catalysts to reduce the concentration of one or more compounds having an oxygen-containing heterocycle having a carbon-carbon double bond in the ring in the crude alcohol, the crude alcohol in which the concentration of said compounds having an oxygen-containing heterocycle having a carbon-carbon double bond in the ring is 200 weight ppm or lower is fed to the purification step.

* * * * *